US00PP08300P

United States Patent [19]

VandenBerg

[11] Patent Number: Plant 8,300

[45] Date of Patent: Jul. 13, 1993

[54] CHRYSANTHEMUM PLANT NAMED ROBIN

[75] Inventor: Cornelis P. VandenBerg, Salinas, Calif.

[73] Assignee: Yoder Brothers, Inc., Barberton, Ohio

[21] Appl. No.: 745,702

[22] Filed: Aug. 16, 1991

[51] Int. Cl.[5] ..... A01H 5/00

[52] U.S. Cl. ..... Plt./79

[58] Field of Search ..... Plt./76, 79

[56] References Cited

U.S. PATENT DOCUMENTS

P.P. 1,307 9/1954 Boerner ..... Plt. 82

OTHER PUBLICATIONS

Plant Patent Directory, 1990, by the American Association of Nurserymen, p. 36; Numerical Listing of Patents.

*Primary Examiner*—Howard J. Locker

*Attorney, Agent, or Firm*—Foley & Lardner

[57] ABSTRACT

A Chrysanthemum plant named Robin particularly characterized by its flat capitulum form; pompon capitulum type; orange-bronze ray floret color; diameter across face of capitulum of 38 to 41 mm when fully opened; spreading and prolific branching pattern, with 6 to 9 breaks after pinch when grown outside under natural daylength in fall flowerings; natural season flower date of August 24 to 28 when planting rooted cuttings on June 21 to 23 in Salinas, Calif., and of September 22 to 24 when planting rooted cuttings June 15 to June 18 in Hightstown, N.J.; flowering response of 45 to 47 days after rooting in no light/no shade programs in spring in Salinas; plant height at flowering time of 28 to 30 cm when grown in fall under natural daylength with no growth regulators in New Jersey, and of 14 to 15 cm when grown in 10 cm pots in spring with 1 application of 2500 ppm B-9 SP; and durable, uniform performance.

3 Drawing Sheets

The present invention comprises a new and distinct cultivar of Chrysanthemum, botanically known as *Dendranthema grandiflora,* and referred to by the cultivar name Robin.

Robin, identified as 9351 (88-267001), was originated from a cross made by Cornelis P. VandenBerg in a controlled breeding program in Salinas, Calif., in 1988.

The female parent of Robin was the cultivar identified as Ginger, disclosed in U.S. Plant Pat. No. 6,403, and described as a flat decorative garden mum with an orange ray flower color and a bronze-red center of the flower; flower diameter of 57 to 64 mm; natural season flower date of August 24 to 28 in Salinas, Calif., and of September 24 to October 1 in Hightstown, N.J.; a flowering response in spring of 43 to 46 days; plant height of 33 to 41 cm in fall natural season flowerings in New Jersey, and of 18 to 20 cm in spring flowerings in 10 cm pots with 1 to 2 applications of 2500 ppm B9-SP in Salinas.

The male parent of Robin was the cultivar identified as 8315 (85-125002), referred to as Megan and described as a spray pot mum and garden mum with a flat capitulum form; a decorative capitulum type with many disc florets; a red-purple ray floret color; a diameter across the face of capitulum of 44 to 54 mm when fully opened; a plant height of 30 to 36 cm from soil line at time of flowering based on June 14 to 16 planting in Hightstown, N.J.; a spreading and prolific branching pattern, averaging 7 to 8 branches per plant after pinch; a natural season flower date of August 23 to 29 in Salinas, Calif., and of September 26 to October 29 in Hightstown, N.J.; and a photoperiodic flowering response to short days of 38 to 49 days in photoperiodic controlled flowering programs.

Robin was discovered and selected as one flowering plant with the progeny of the stated cross by Cornelis P.

VandenBerg in November 1988, in a controlled environment in Salinas, Calif.

The first act of asexual reproduction of Robin was accomplished when vegetative cuttings were taken from the initial selection in January 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Robin are firmly fixed and are retained through successive generations of asexual reproduction.

Robin has not been observed under all possible environmental conditions. The phenotype may vary somewhat with variations in environment such as temperature, light intensity and daylength, without, however, any variance in the genotype.

The following observations, measuremnents and comparisons describe plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Robin, which, in combination, distinguish this Chrysanthemum as a new and distinct cultivar:

1. Flat capitulum form.
2. Pompon capitulum type.
3. Orange-bronze ray floret color.
4. Diameter across face of capitulum of 38 to 41 mm when fully opened.

5. Branching pattern is spreading and prolific, with 6 to 9 breaks after pinch when grown outside under natural daylength in fall flowerings.

6. Natural season flower date of August 24 to 28 when planting rooted cuttings on June 21 to 23 in Salinas, Calif., and of September 22 to 24 when planting rooted cuttings June 15 to June 18 in Hightstown, N.J.

7. Flowering response of 45 to 47 days after rooting in no light/no shade programs in spring in Salinas.

8. Plant height at flowering time of 28 to 30 cm when grown in fall under natural daylength with no growth regulators in New Jersey, and of 14 to 15 cm when grown in 10 cm pots in spring with 1 application of 2500 ppm B-9 SP.

9. Durable, uniform performance.

The accompanying photographic drawings show typical inflorescence and leaf characteristics of Robin, with the colors being as nearly true as possible with illustrations of this type.

Sheet 1 is a color photograph of Robin grown as a pinched spray pot mum with 1 cutting in a 10 cm. pot.

Sheet 2 is a black and white photograph of three views of the inflorescence of Robin.

Sheet 3 is a black and white photograph showing the upper and under sides of the leaves of Robin at 3 stages of development (mature, intermediate and immature). In sheets 2 and 3 a measuring tape in centimeters has been added.

Of the commercial cultivars known to the inventor, the most similar in comparison to Robin is the cultivar identified as Mirage, disclosed in U.S. Plant Pat. No. 6,388. Reference is made to attached Chart A, which compares certain characteristics of Robin to the same characteristics of Mirage.

Similar traits are capitulum form and type, diameter across face of capitulum, and branching pattern. Natural season flowering response in New Jersey, controlled flowering response in California, and plant height in natural season fall flowering in New Jersey of Robin and Mirage are in the same range. Although the ray floret color of both Robin and Mirage is described as orange-bronze, Robin has a warmer orange-bronze ray floret color, with a better color retention than Mirage. Robin has a slower natural season flowering response in the fall in Salinas by 2–3 days, and a shorter plant height in 10 cm pots in spring flowerings in Salinas. In addition, Robin has an overall better, more cushion-like plant habit than Mirage, with a better display of flowers in fall flowerings.

In the following description color references are made to the Royal Horticultural Society Colour Chart. The actual color of Robin is not represented in the R.H.S. Colour Chart, and the values given are those believed closest to the actual color of Robin. The color values were determined on plant material grown as a pinched spray pot mum in a 10 cm pot in Salinas, Calif. on Apr. 11, 1991.

Classification:

*Botanical.*—*Dendranthema grandiflora* cv. Robin.

*Commercial.*—Flat pompon spray pot mum and garden mum.

INFLORESCENCE

A. Capitulum:

*Form.*—Flat.

*Type.*—Pompon.

*Diameter across face.*—38 to 41 mm when fully opened.

B. Corolla of ray florets:

*Color (general tonality from a distance of three meters).*—Orange-bronze.

*Color (upper surface).*—22A, overcast with 169D.

*Color (under surface).*—22A, overcast with 169D.

*Shape.*—Longitudinally straight, concave cross section.

Corolla of disc florets:

*Color (mature).*—14B.

*Color (immature).*—144B.

D. Reproductive organs:

*Androecium.*—Present on disc florets only; very few, no pollen.

*Gynoecium.*—Present on both ray and disc florets.

PLANT

A. General appearance:

*Height.*—25 to 30 cm when grown in fall under natural daylength in New Jersey with no growth regulators, and of 14 to 15 cm when grown in 10 cm pots in spring in Salinas with 1 application of 2500 ppm B-9 SP.

*Branching pattern.*—Spreading and prolific, with 6 to 9 breaks after pinch when grown outside under natural daylength in fall flowerings.

B. Foliage:

*Color (upper surface).*—147A.

*Color (under surface).*—147B.

*Shape.*—See photograph.

CHART A

| CHARACTERISTIC | ROBIN | MIRAGE |
|---|---|---|
| Ray floret color | Orange-bronze | Orange-bronze |
| Capitulum form and type | Flat Pompom | Flat Pompom |
| Diameter across face of capitulum | 38 to 41 mm | 38 to 41 mm |
| Branching pattern | Spreading and prolific | Spreading and prolific |
| Natural season flower date: | | |
| in Salinas, CA | Aug. 24 to 28 | Aug. 21 to 26 |
| in Hightstown | Sept. 22 to 24 | Sept. 21 to 26 |
| Controlled response | 45 to 47 days | 45 to 49 days |
| Plant height: | | |
| in natural season fall | 25 to 30 cm | 20 to 30 cm |
| in 10 cm pots spring | 14 to 15 cm | 15 to 20 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Robin, as described and illustrated.

* * * * *

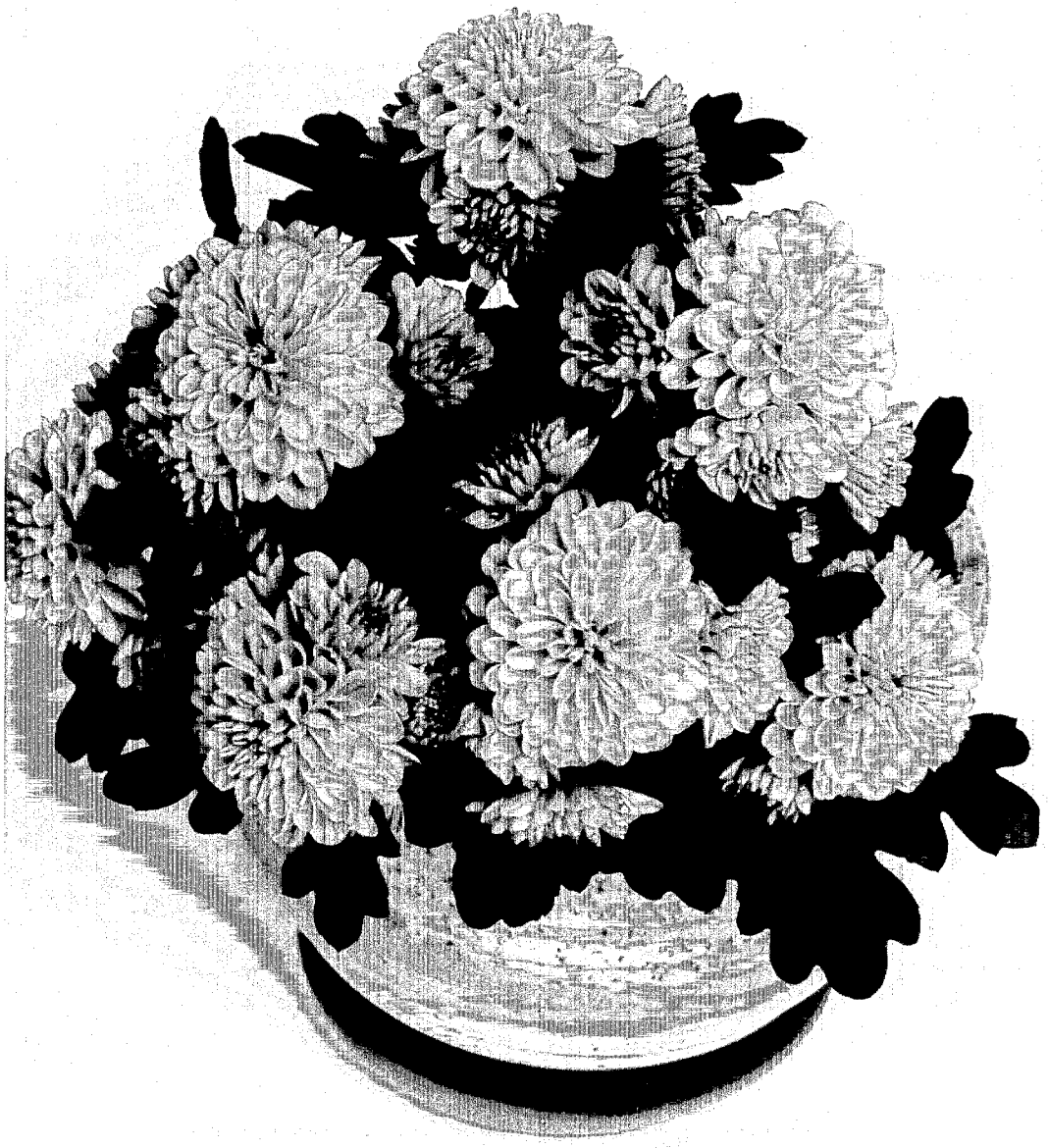

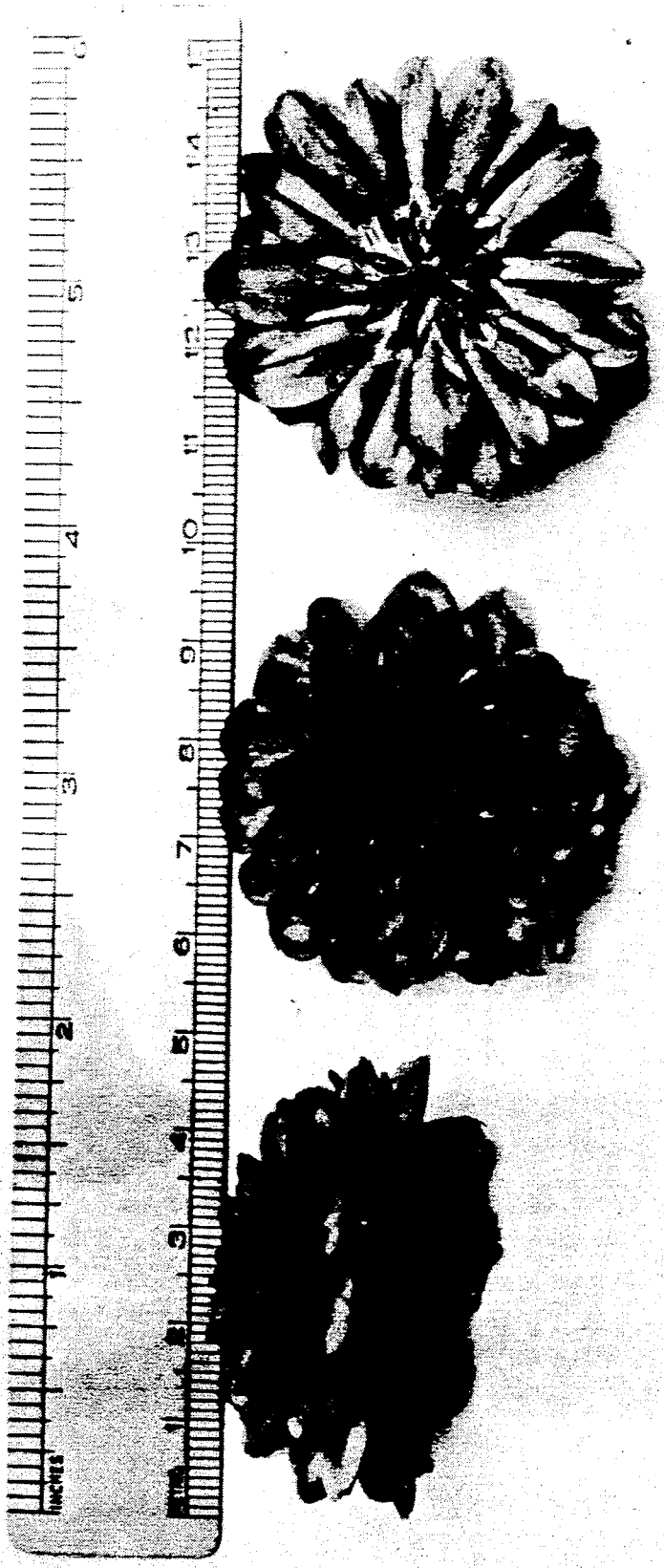
INCHES

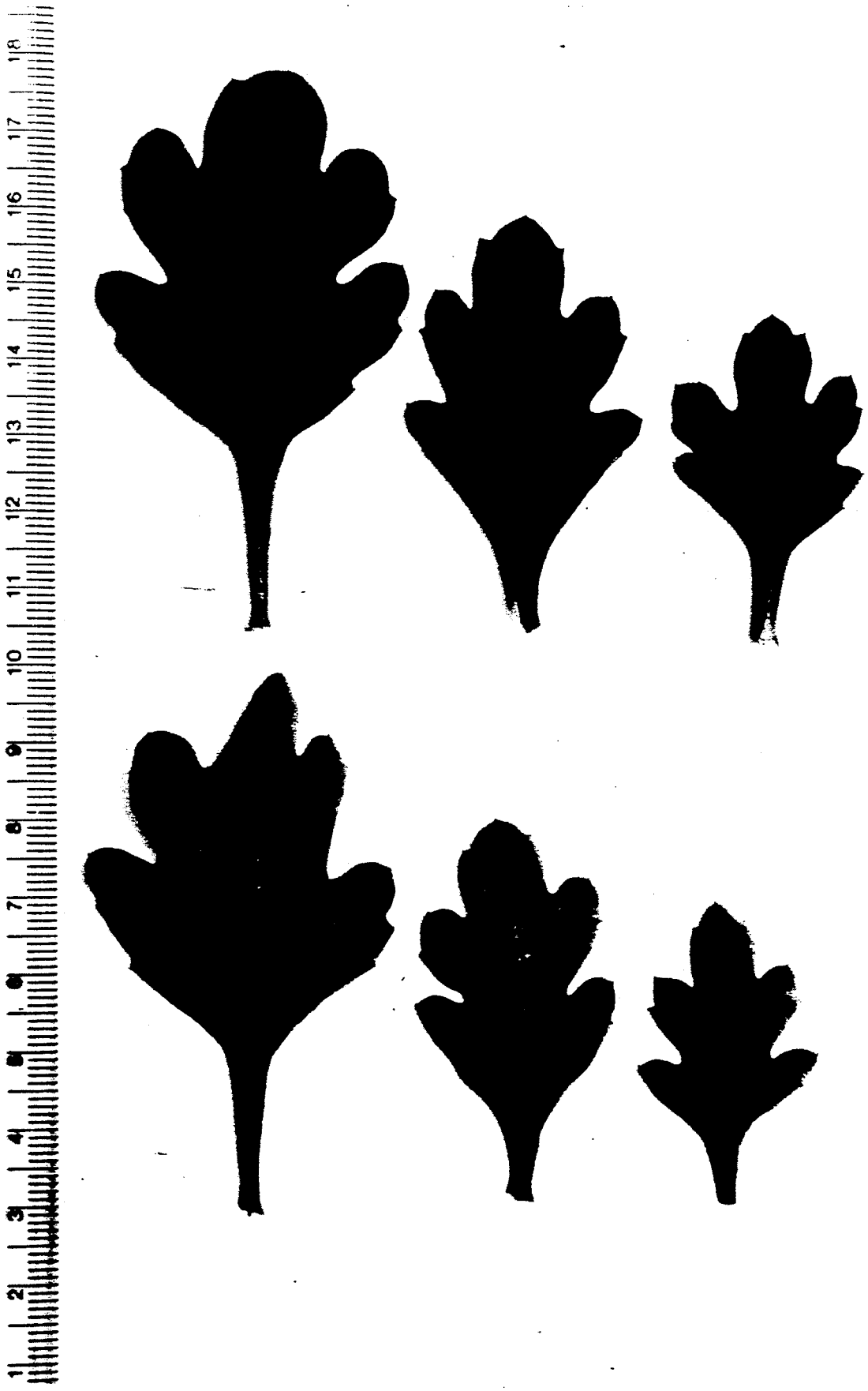
1
2
3
4
5
6
7
8
9
10
11
12
13
14
15
16
17
18